(12) United States Patent
Kim et al.

(10) Patent No.: US 10,221,412 B2
(45) Date of Patent: Mar. 5, 2019

(54) MULTIPLEX MICROFLUIDIC DEVICE FOR SELECTING NUCLEIC ACID APTAMERS, AND HIGH THROUGHPUT SELECTION METHOD FOR NUCLEIC ACID APTAMERS USING SAME

(75) Inventors: So Youn Kim, Seoul (KR); Ji-Young Ahn, Seoul (KR); Minjoung Jo, Seoul (KR); Tae Kyung Kim, Busan (KR)

(73) Assignees: PCL, INC., Gyeonggi-Do (KR); DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 1152 days.

(21) Appl. No.: 13/877,862

(22) PCT Filed: Oct. 5, 2011

(86) PCT No.: PCT/KR2011/007367
§ 371 (c)(1),
(2), (4) Date: Jun. 24, 2013

(87) PCT Pub. No.: WO2012/047015
PCT Pub. Date: Apr. 12, 2012

(65) Prior Publication Data
US 2013/0274113 A1    Oct. 17, 2013

(30) Foreign Application Priority Data
Oct. 5, 2010 (KR) .................... 10-2010-0096685

(51) Int. Cl.
| C12N 15/10 | (2006.01) |
| C40B 30/04 | (2006.01) |
| C12N 15/11 | (2006.01) |
| C12N 15/115 | (2010.01) |
| G01N 33/53 | (2006.01) |

(52) U.S. Cl.
CPC ........ *C12N 15/1048* (2013.01); *C12N 15/111* (2013.01); *C12N 15/115* (2013.01); *G01N 33/5308* (2013.01); *C12N 2310/16* (2013.01); *C12N 2320/11* (2013.01); *C12N 2320/13* (2013.01); *G01N 2500/00* (2013.01)

(58) Field of Classification Search
CPC .................................................... C12N 15/10
USPC ........................................................ 506/1
See application file for complete search history.

(56) References Cited

U.S. PATENT DOCUMENTS

| 5,607,646 | A | 3/1997 | Okano et al. | |
| 7,744,762 | B2 * | 6/2010 | Lazar ..................... | H01J 49/04 |
| | | | | 210/198.2 |
| 2002/0079219 | A1 * | 6/2002 | Zhao ................. | B01L 3/502707 |
| | | | | 204/451 |
| 2004/0248167 | A1 | 12/2004 | Quake et al. | |
| 2005/0064465 | A1 | 3/2005 | Dettloff et al. | |
| 2009/0000690 | A1 * | 1/2009 | Oldham ............ | B01L 3/502723 |
| | | | | 141/4 |
| 2009/0176230 | A1 * | 7/2009 | McBride ........... | B01L 3/502707 |
| | | | | 435/6.19 |
| 2012/0028811 | A1 * | 2/2012 | Craighead ......... | B01L 3/502753 |
| | | | | 506/1 |
| 2013/0203634 | A1 * | 8/2013 | Jovanovich ....... | B01L 3/502738 |
| | | | | 506/26 |

FOREIGN PATENT DOCUMENTS

| WO | 2010019969 A1 | 2/2010 | |
| WO | WO 2010019969 A1 * | 2/2010 | ........ B01L 3/502753 |

OTHER PUBLICATIONS

Park et al., Selection and Elution of Aptamers Using Nanoporous Sol-Gel Arrays With Integrated Microheaters, Lab Chip, 2009, 9, 1206-1212.*
Sun et al., A Heater-Integrated Transparent Microchannel Chip for Continuous-Flow PCR, Sensors and Actuators B, 2002, 84, 283-289. (Year: 2002).*
Eulberg, D., et al., "Development of an automated in vitro selection protocol to obtain RNA-based aptamers: identification of a biostable substance P antagonist", "Nucleic Acids Research", Mar. 3, 2005, pp. 1-10, vol. 33, No. 4: e45.
Hybarger, G., et al., "A microfluidic SELEX prototype", "Anal. Bioanal. Chem.", Nov. 29, 2005, pp. 191-198, vol. 384.
Kim, Y., et al., "Aptamer-based biosensor technology", "News & Information for Chemical Engineers", 2008, pp. 690-695, vol. 26, No. 6.
Kim, Y., et al., "Aptamer-based biosensor technology", "News & Information for Chemical Engineers", 2008, pp. 690-695 (English Translation Paragraph 1, p. 690), vol. 26, No. 6.
Windbichler, N., et al., "Isolation of specific RNA-binding proteins using the streptomycin-binding RNA aptamer", "Nature Protocols", Jun. 27, 2006, pp. 638-641, vol. 1, No. 2.

* cited by examiner

*Primary Examiner* — Amy M Bunker
(74) *Attorney, Agent, or Firm* — Hultquist, PLLC; Steven J. Hultquist

(57) ABSTRACT

The present invention relates to a multiplex microfluidic device for selection of nucleic acid aptamers and a method for high-throughput selection of nucleic acid aptamers using the same, and more particularly to a multiplex microfluidic device (SELEX lap-on-a-chip) that uses an improved multiplex platform in place of the development of an aptamer for a single target and to a method for high throughput selection of aptamers using the same together with high-throughput sequencing. A multiplex microfluidic device according to the present invention can simultaneously detect aptamers for a plurality of targets, and it can greatly increase the screening throughput and greatly shorten the process time compared to conventional multiplex techniques. Particularly, when a process for selecting aptamers is performed using the device of the invention together with a high-throughput sequencing method, the number of target binding/elution/amplification rounds can be greatly reduced, and the process can be performed in an automated manner. Thus, the device of the invention is highly useful.

18 Claims, 15 Drawing Sheets

FIG. 2
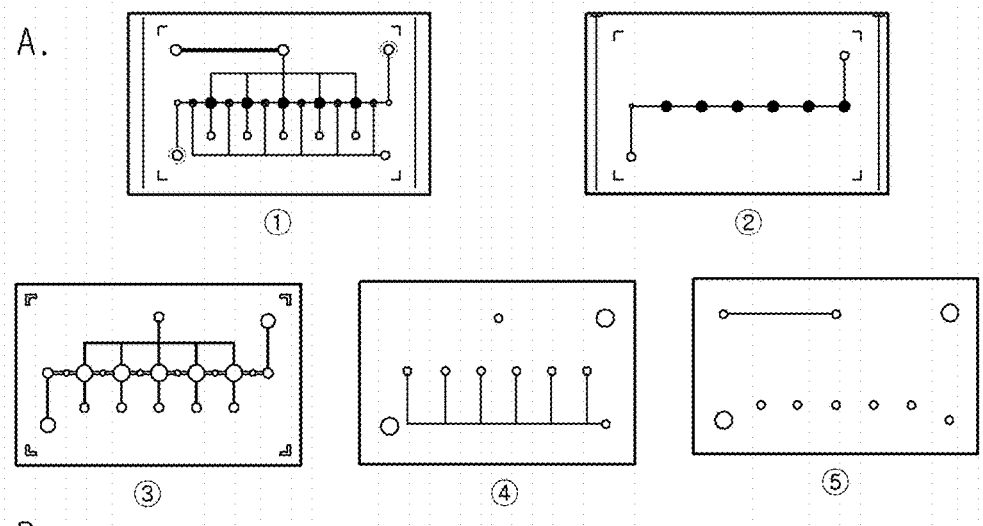
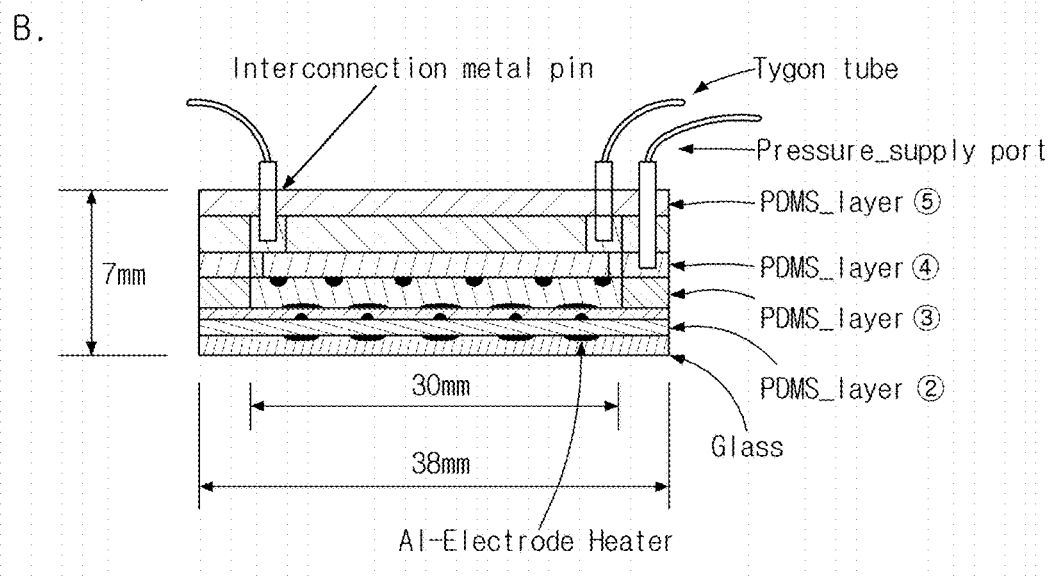

FIG. 14
A.
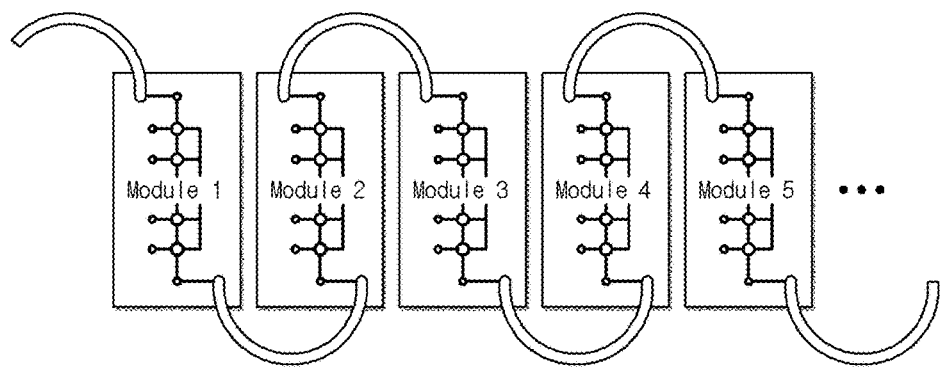
B.
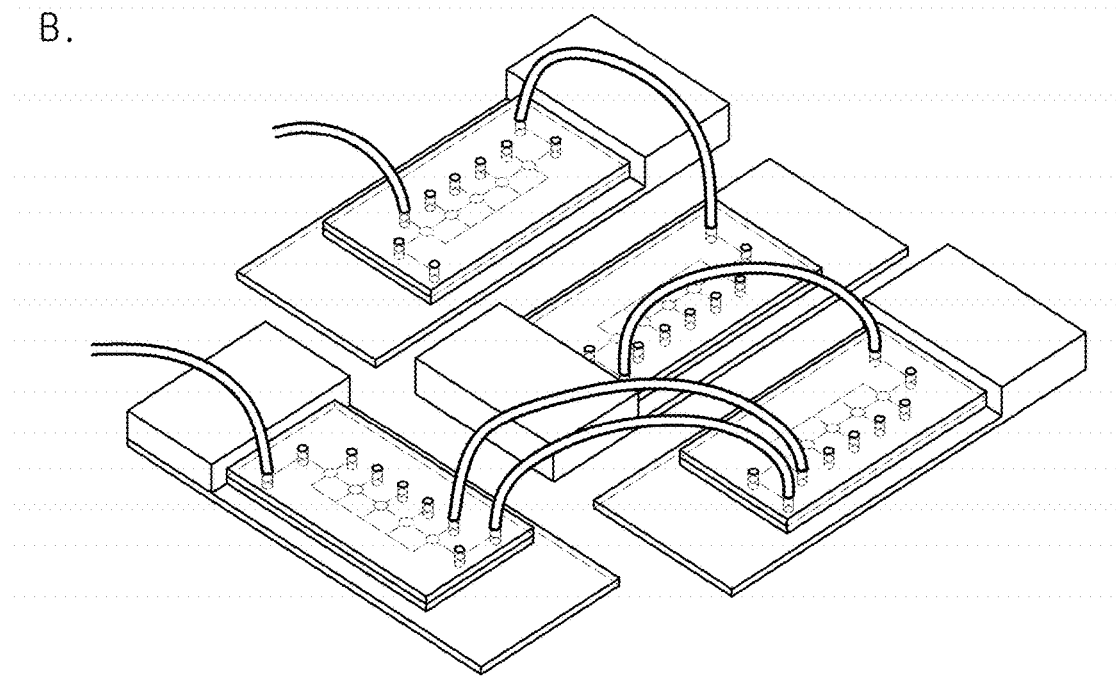

MULTIPLEX MICROFLUIDIC DEVICE FOR SELECTING NUCLEIC ACID APTAMERS, AND HIGH THROUGHPUT SELECTION METHOD FOR NUCLEIC ACID APTAMERS USING SAME

CROSS-REFERENCE TO RELATED APPLICATIONS

This application is a U.S. national phase under the provisions of 35 U.S.C. § 371 of International Patent Application No. PCT/KR11/07367 filed Oct. 5, 2011, which in turn claims priority of Korean Patent Application No. 10-2010-0096685 filed Oct. 5, 2010. The disclosures of such international patent application and Korean priority patent application are hereby incorporated herein by reference in their respective entireties, for all purposes.

TECHNICAL FIELD

The present invention relates to a multiplex microfluidic device for selection of nucleic acid aptamers and a method for high-throughput selection of nucleic acid aptamers using the same, and more particularly to a multiplex microfluidic device (SELEX lap-on-a-chip) that uses an improved multiplex platform in place of the previous development method of an aptamer for a single target and to a method for high throughput selection of nucleic acid aptamers using the same together with high-throughput sequencing.

BACKGROUND ART

Aptamer is single-stranded DNA or RNA molecule. The aptamer is a small single-stranded oligonucleotide that can bind specifically to its target with high affinity. The aptamer can be used as a biosensor element capable of binding to a molecule in a detection/analysis system, and thus has been recognized as a substitute for antibody. Particularly, the aptamers can be used as molecules targeting various organic and inorganic materials, including toxins, unlike antibodies, and once an aptamer that binds specifically to a certain material is isolated, it can be consistently reproduced at low costs using automated oligomer synthesis methods. Since an aptamer-based biosensor of measuring a target protein using a fluorescence-labeled aptamer was first developed in 1996, various aptamer biosensors have been developed based on the advantages and structural properties of the aptamer (Yeon-Seok KIM & Man-Bock G U, NICE, 26(6):690, 2008).

To isolate such aptamers, a SELEX (Systematic Evolution of Ligands by EXponential enrichment) process has been used. However, in this SELEX process, aptamers for only single target molecule can be isolated, and an amplification/isolation process should be repeated 10 times or more until aptamers having high affinity are selected or a smaller number of nucleic acids remain, and also an affinity test is additionally required. Thus, the SELEX process has shortcomings in that it requires a large amount of time to develop a new aptamer and is complicated. Due to these shortcomings, there has been a demand for a new process for aptamer selection, which can simultaneously isolate aptamers for two or more target substances in a simpler and faster manner. In addition, the introduction of an automated process for aptamer selection has been demanded.

In recent years, several microfluidic techniques have been introduced for faster SELEX processes, and efforts have been made to shorten the time taken to isolate aptamers from several months/several weeks to several days (Hybarget, et al., *Anal. Bioanal. Chem.*, 384:191, 2006; Windbichler, et al., *Nat. Protoc.*, 1:637, 2006; Eulberg, et al., *Nucleic Acids Research*, 33:e45, 2005). However, such methods are not suitable as small-scale processes for multiplexed selection of aptamers. In connection with this, the present inventors developed a microfluidic device that employs a multiplex technique (see PCT/US2009/054097). However, this microfluidic device has shortcomings in that several aptamers cannot be simultaneously isolated, and that aptamers bound to target molecules can only be sequentially be isolated and also that means for isolating aptamers are limited. Thus, there has been a demand for the development of a new device and process, which use a new method suitable for shortening the process time and automating the overall process.

Accordingly, the present inventors have made extensive efforts to provide a new multiplex microfluidic device, which has improved efficiency and can be automated, and a method for high-throughput selection of aptamers using the same, and as a result, have found that a module assembly manufactured by constructing microfluidic device modules having a main microfluidic channel and a separate elution channel or tube and connecting the modules to each other can simultaneously isolate aptamers for several tens or hundreds of target substances in several tens or hundreds of chambers and can be automated by being connected to a high-throughput sequencing or high-throughput affinity test device, thereby completing the present invention.

SUMMARY OF INVENTION

It is an object of the present invention to provide a novel and improved multiplex microfluidic device capable of simultaneously selecting a plurality of aptamers.

Another object of the present invention is to provide a novel method for selection of aptamers, which can screen a plurality of aptamers in a faster manner than conventional methods and can be automated.

To achieve the above objects, the present invention provides a multiplex microfluidic device for selection of nucleic acid aptamers, which comprises:

(a) a substrate comprising a binding channel that connects an inlet port to an outlet port;

(b) a plurality of target molecule-binding regions formed in the binding channel;

(c) a plurality of elution channels connected to the plurality of target molecule-binding regions, respectively; and (d) a valve on/off system.

The present invention also provides a multiplex microfluidic device for selection of aptamers, which comprise:

(a) a substrate comprising a binding channel that connects an inlet port to an outlet port;

(b) a plurality of target molecule-binding regions formed in the binding channel; and (c) a connection region that connects the plurality of target molecule-binding regions to each other.

The present invention also provides a multiplex chip for selection for aptamers, which comprises two or more microfluidic devices as described above as a module, wherein the modules are connected to each other by a connection region.

The present invention provides a method for high-throughput selection of nucleic acid aptamers, which comprises the steps of:

(a) introducing a pool of nucleic acids having randomized sequences into the binding channel of the above multiplex fluidic device to react with target molecules of target molecule-binding regions in the binding channels;

(b) removing nucleic acids, unbound to the target molecules, from the multiplex fluidic device;

(c) eluting nucleic acids, bound to the target molecules, to elution channels or one end of a connection region in the multiplex fluidic device;

(d) collecting and amplifying the nucleic acids eluted in step (c);

(e) introducing the nucleic acids, amplified in step (d), into the binding channel of the multiplex fluidic device, and repeatedly performing steps (a) to (d), wherein amplification of the eluted nucleic acids is not performed in a final repeat round; and (f) selecting nucleic acids, eluted in the final repeat round, as aptamers.

The present invention also provides a kit for high-throughput selection of aptamers, which comprises the above multiplex microfluidic device.

The present invention also provides a method of analyzing nucleic acids, selected using the multiplex fluidic device, by a high-throughput sequencing method.

Other features and embodiments of the present invention will be more apparent from the following detailed descriptions and the appended claims.

BRIEF DESCRIPTION OF THE DRAWINGS

FIG. 2 is a schematic view showing a 5-plex microfluidic device comprising a pneumatic valve on/off system.

In FIG. 3, "pneumatic valve 1" is used to separate the binding channel between the plurality of target molecule-binding regions to elute target molecule-bound nucleic acids, and "pneumatic valve 2" is to operate the switch between the binding channel and elution channels.

FIG. 4(a) is a 5-plex microfluidic device; FIG. 4(b) is a photograph showing blue ink (binding solution containing aptamers to bind to target molecules) is injected into a main binding channel; FIG. 4(c) is a photograph showing that a washing process is performed using a washing solution; FIG. 4(d) is a photograph showing that red ink (elution solution) is injected into elution channels; FIG. 4(e) is a photograph showing that a fluid is injected along channels in a valve-on state; FIG. 4(f) is a photograph showing that the fluid flows into each elution channel in a valve-on state.

FIG. 14A is a schematic view showing a multiplex chip obtained by connecting modules to each other by a tube; and FIG. 14B is a photograph showing actual modules connected to each other.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

The definition of main terms used in the detailed description of the invention is as follows.

As used herein, the term "nucleic acid" means either DNA, RNA, single-stranded or double-stranded and any chemical modifications thereof, provided only that the modification does not interfere with amplification of selected nucleic acids. Examples of the modification include, but are not limited to, backbone modifications, methylations, unusual base-pairing combinations, substitution of 5-bromouracil, and the like.

As used herein, the term "aptamer" refers to a small single-stranded oligonucleotide that can bind specifically to its target with high affinity.

A target molecule that is used in the present invention may be a protein or polypeptide, a carbohydrate, a lipid, a pharmaceutical agent, a low-molecular-weight material, an organic non-pharmaceutical agent, or a macromolecular complex such as a cell. Herein, the term "low-molecular-weight material" is meant to include non-polar low-molecular-weight compounds such as bisphenol A.

As used herein, the term "target molecule-binding region" refers to a reaction chamber which has a target molecule bound thereto by a sol-gel composition, a bead or the like so that an aptamer can bind to the target molecule.

As used herein, the term "microfluidic device" refers to a device that can be used to control or manipulate fluids with volumes on the order of µl, nL, pL, fL or the like.

Figure 1:
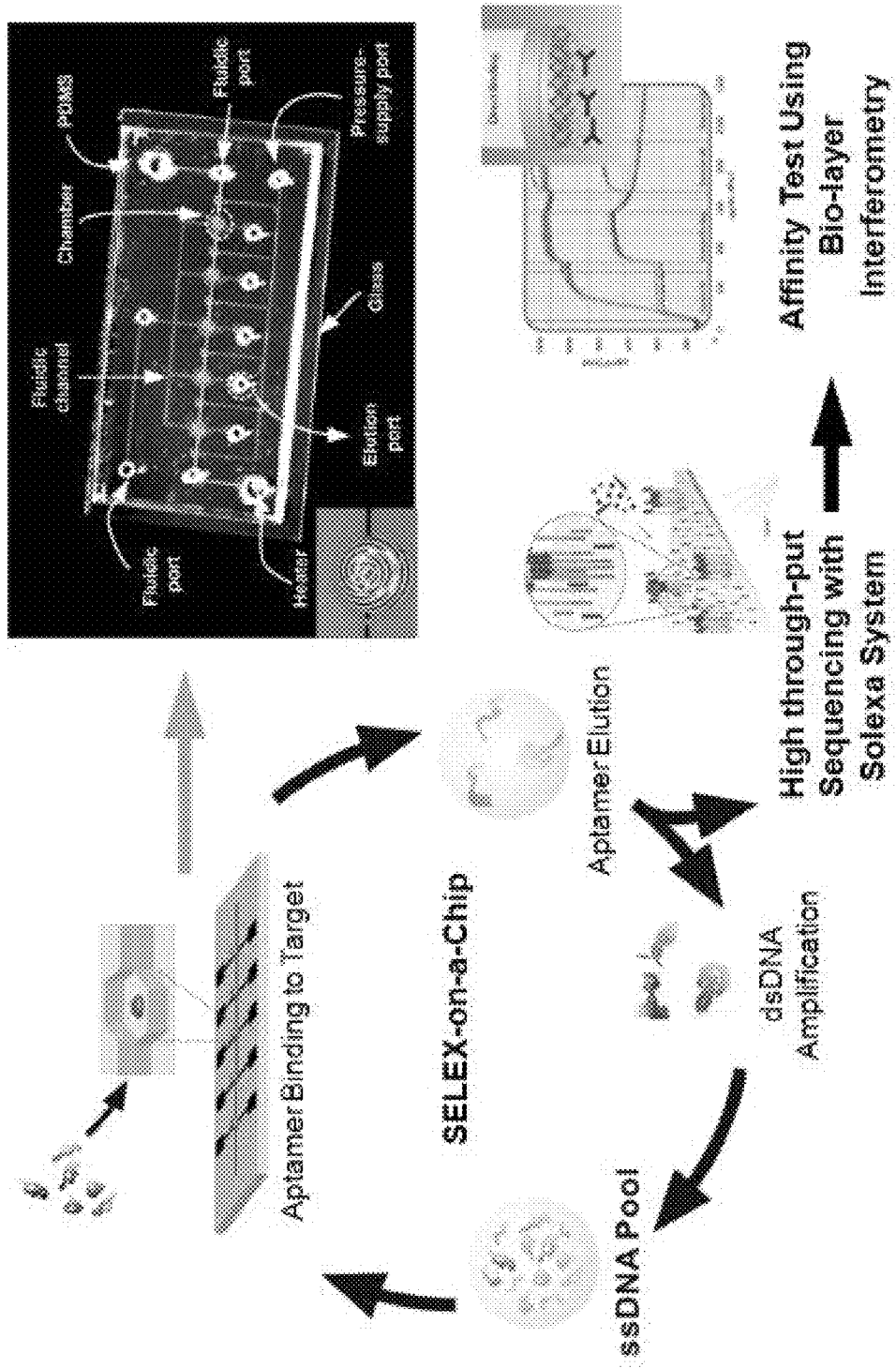
FIG. 1 is a schematic view showing a method for selection of aptamers according to the present invention.

In one aspect, the present invention is directed to a multiplex microfluidic device for selection of nucleic acid aptamers, which can be applied to an improved SELEX (Systematic Evolution of Ligands by Exponential Enrichment) process as shown in FIG. 1.

The multiplex microfluidic device for selection of nucleic acid aptamers according to the present invention comprises:

(a) a substrate comprising a binding channel that connects an inlet port to an outlet port;

(b) a plurality of target molecule-binding regions formed in the binding channel;

(c) a plurality of elution channels connected to the plurality of target molecule-binding regions, respectively;

(d) a valve on/off system.

In the present invention, a plurality of target molecule-binding regions are formed in a fluid channel extending between an inlet port and an outlet port, and thus the fluid channel extending between the inlet port and the outlet port is defined as a binding channel. In addition, fluid channels which are respectively connected to the target molecule-binding regions to elute target molecule-bound nucleic acid molecules from the target molecule-binding regions are defined as elution channels.

The present invention is characterized in that a plurality of target molecule-binding regions are formed in one binding channel. Herein, the target molecules that are included in the target molecule-binding regions may be the same target molecules or two or more different target molecules. Preferably, the target molecules may be different target molecules, and in this case, the target molecule-binding region, that is, a chamber in which the target molecule binds to the introduced nucleic acid pool, is connected to other chambers by the binding channel, and thus when a pool of nucleic acids having randomized sequences is added to the inlet port of the binding channel, the nucleic acid pool can enter each chamber and bind to several nucleic acid molecules. Thus, the competition of aptamers for each target molecule can be induced so that aptamers having high affinity can be screened.

In the present invention, the binding channel and the target molecule-binding region may be formed by a substrate lid which is deposited on the surface of the substrate. In addition, the plurality of elution channels may also be formed by a substrate lid which is deposited on the surface of the chip. When the nucleic acids bound to the target molecules are eluted from the target molecule-binding regions, the volume and rate of the eluted solutions can be made constant by equalizing the lengths of the elution channels.

Meanwhile, the valve on/off system can be operated so that a fluid flows between the plurality of target molecule-binding regions through the binding channel during the binding reaction, and after completion of the binding reaction, the fluid does not flow between the plurality of target molecule-binding regions through the binding channel and nucleic acids bound to the target molecules of the target molecule-binding regions can be eluted to the elution channels connected to the target molecule-binding regions. Herein, the valve on/off system can automatically control the switch between the binding channel and the elution channels in the multiplex microfluidic chip and may include two or more devices, that is, two or more valves, so that the valves can be operated in different manners. For example, the valve on/off system may include a valve for controlling the fluid flow in the binding channel and a valve for eluting fluids containing nucleic acids bound to the target molecules to the elution channels.

This valve system can control and optimize the speed and flow rate of fluids to reduce the pressure in the adhesion portion between the substrate lid and the substrate (chip) to thereby minimize the leakage of fluids.

The valve on/off system may be any one of valves (pressure valves, frequency control valves, micro-valves and directional corks) that are driven by heat, air pressure, thermopneumatic pressure, hydraulic pressure, electrostatic force, electromagnetic force, magnetic force, phase change, piezoelectric pressure or the like, but is not limited thereto, if the valve on/off system may be any valve on/off system that enables a fluid containing the nucleic acid pool to flow through the binding channel during the reaction of the nucleic acid pool having randomized sequences with the target molecules and allows a fluid containing the target molecule-bound nucleic acids to the elution channels when the nucleic acids bound to the target molecules are eluted.

Herein, the pressure valve may change the flow of fluids using pressure such as hydraulic pressure, air pressure and the like, and the micro-valve may include a micro-sized 2-way or 3-way valve so as to enable fluids to flow to the elution channels or the binding channel. In addition, the system comprising the directional cork is a directional active on/off system and refers to a valve on/off system which is horizontally opened during the reaction of nucleic acids with target molecules so as to allow fluids to flow through the binding channel and allows the bound nucleic acids to be individually eluted vertically through the elution channels.

In one embodiment of the present invention, as shown in FIG. 2, a 5-plex microfluidic device, which comprises a pneumatic valve on/off system and can simultaneously screen aptamers for five target molecules, was prepared. A 5-plex SELEX-on-a-Chip according to the present invention comprises a base portion comprising a metal electrode as a heater, and a lid portion in which chambers, channels and a valve on/off system (pressure valve) are formed (① of FIG. 2). The base portion capable of serving as a heater which can elute nucleic acids bound to target molecules was obtained by coating a chip, which has five heater electrode patterns made of Cr/Au, with PDMS (polydimethylsiloxane) (② of FIG. 2), and the substrate lid has formed thereon and comprises a first layer (③ of FIG. 2) having a channel connecting five chambers to each other, a second layer (④ of FIG. 2) serving as a chip lid and having a pneumatic valve, and a third layer (⑤ of FIG. 2) serving as a support so that fluids and pneumatic pressure can be easily introduced. Herein, the substrate lid was made of PDMS.

The reaction chamber for aptamer-target molecules had a diameter of 1.8 mm, a height of 30 μm and a channel width of 0.28 mm. The chamber for applying air pressure had a diameter of 0.5 mm, a height of 30 μm and a channel width of 0.2 mm. For bonding between for PDMS and PDMS, the surface was treated with plasma under atmospheric pressure to become ultra-hydrophobic and subjected to a bonding process, and the time of exposure to $Ar/O_2$ in the surface treatment was 2 seconds.

Figure 3:
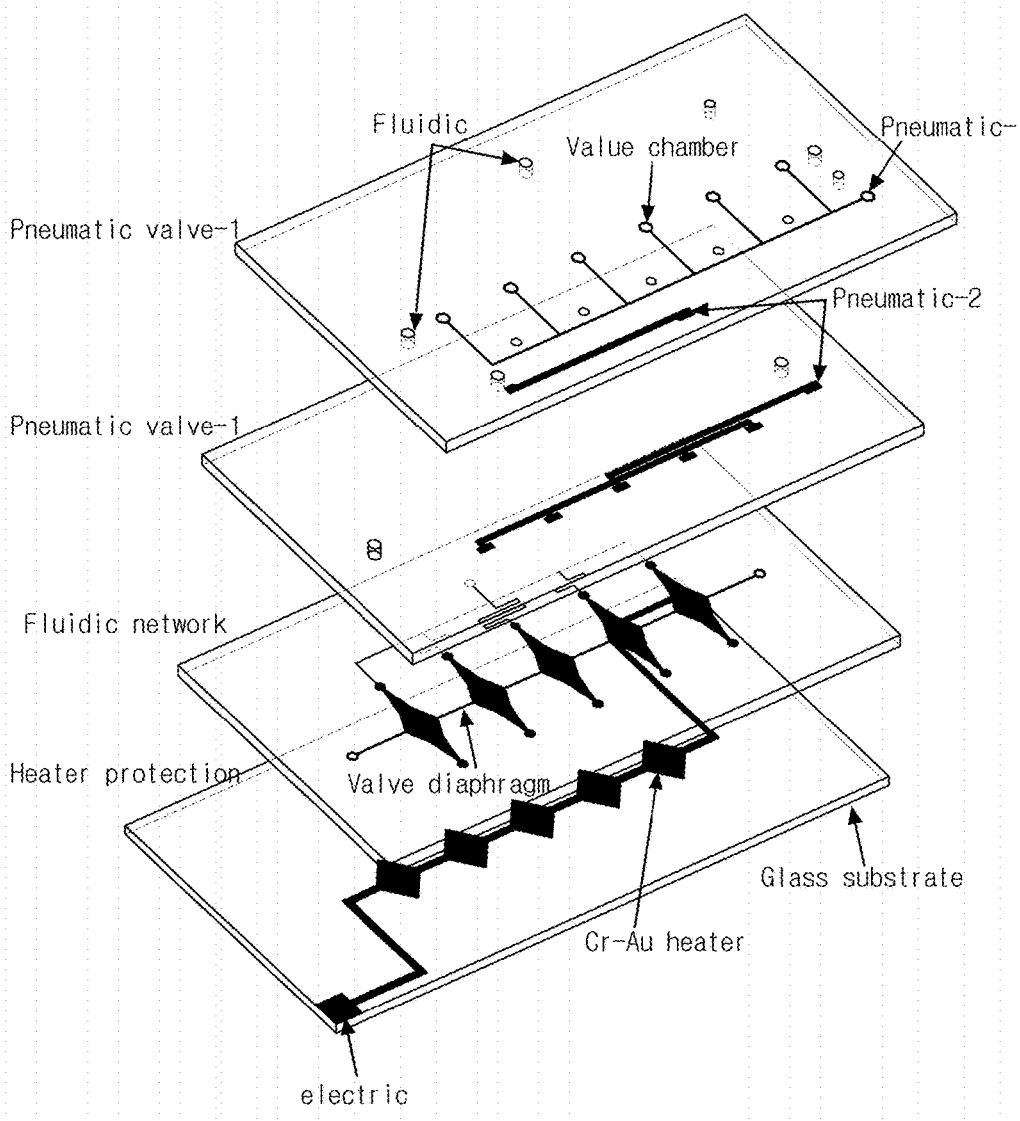
FIG. 3 is a schematic view showing a 5-plex microfluidic device having a valve on/off system including a valve, which is used to separate a binding channel between a plurality of target molecule-binding regions to elute target molecule-bound nucleic acids, and a valve which is used to operate the switch between the binding channel and elution channels.
Figure 4:
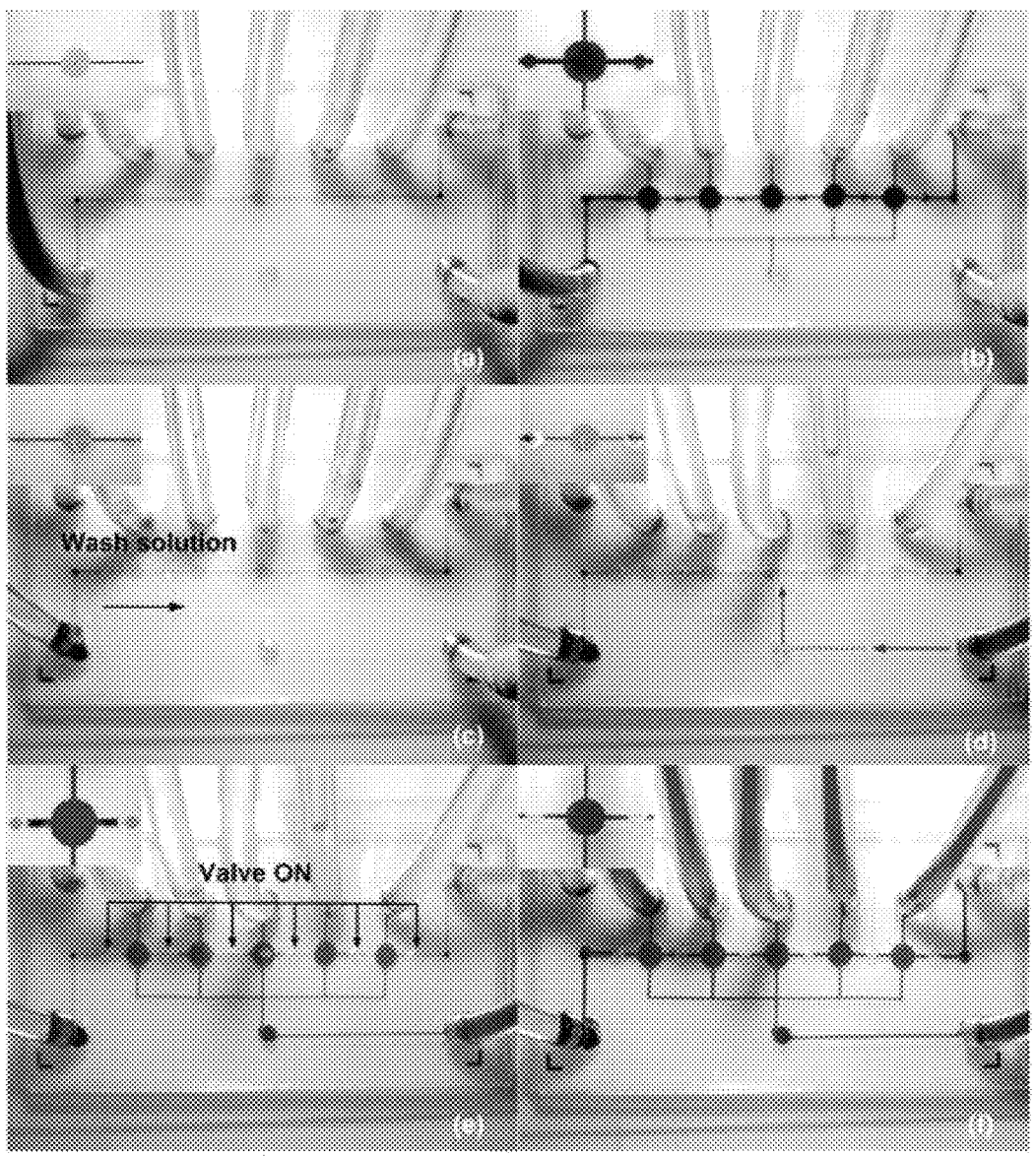
FIG. 4 is a set of photographs showing a flowchart of the device manufactured according to FIG. 2.

The pneumatic value disposed in the channel that connects the target molecule-binding regions (i.e. chambers) to each other can formed such that pneumatic pressure is formed to prevent fluids from flowing between the chambers and that fluids can individually flow to the elution channels. In addition, as shown in FIG. 3, the switch between the binding channel and the elution channels was automatically controlled by a separate valve. In other words, as shown in FIG. 4, when nucleic acids were to be bound to target molecules, the pneumatic valve was opened, a fluid containing a nucleic acid pool could flow through the chambers while the nucleic acids could bind to the target molecules, and when the nucleic acids were to be eluted, the flow of the fluid was blocked by the pneumatic valve, and then the metal electrode portions (chambers) were heated so that the fluid did flow out of each chamber without cross-contamination.

Figure 5:
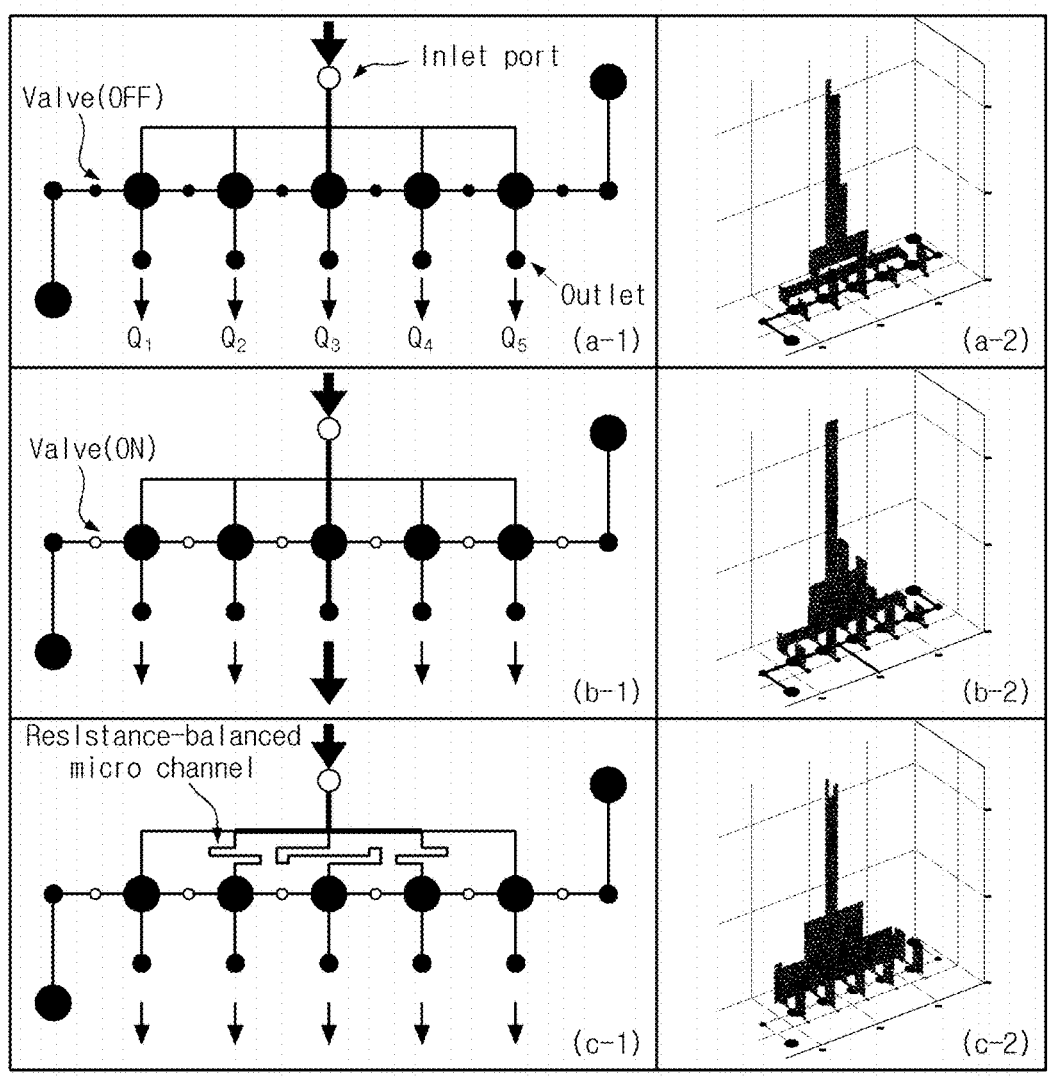
FIG. 5 shows that the volume and elution rate of an elution solution are constant when the lengths of elution channels for eluting bound nucleic acids from a plurality of target molecule-binding regions are equalized.

In addition, in this embodiment, the lengths of the elution channels for eluting the bound nucleic acids from the plurality of target molecule-binding regions were equalized, and as a result, it was found that the volume and elution rate of an elution solution eluted to the elution channels were constant (FIG. 5). Herein, in order to equalize the lengths of the elution channels and the flow rates, resistance (twist of channels) can be introduced in the elution channels.

Figure 6:
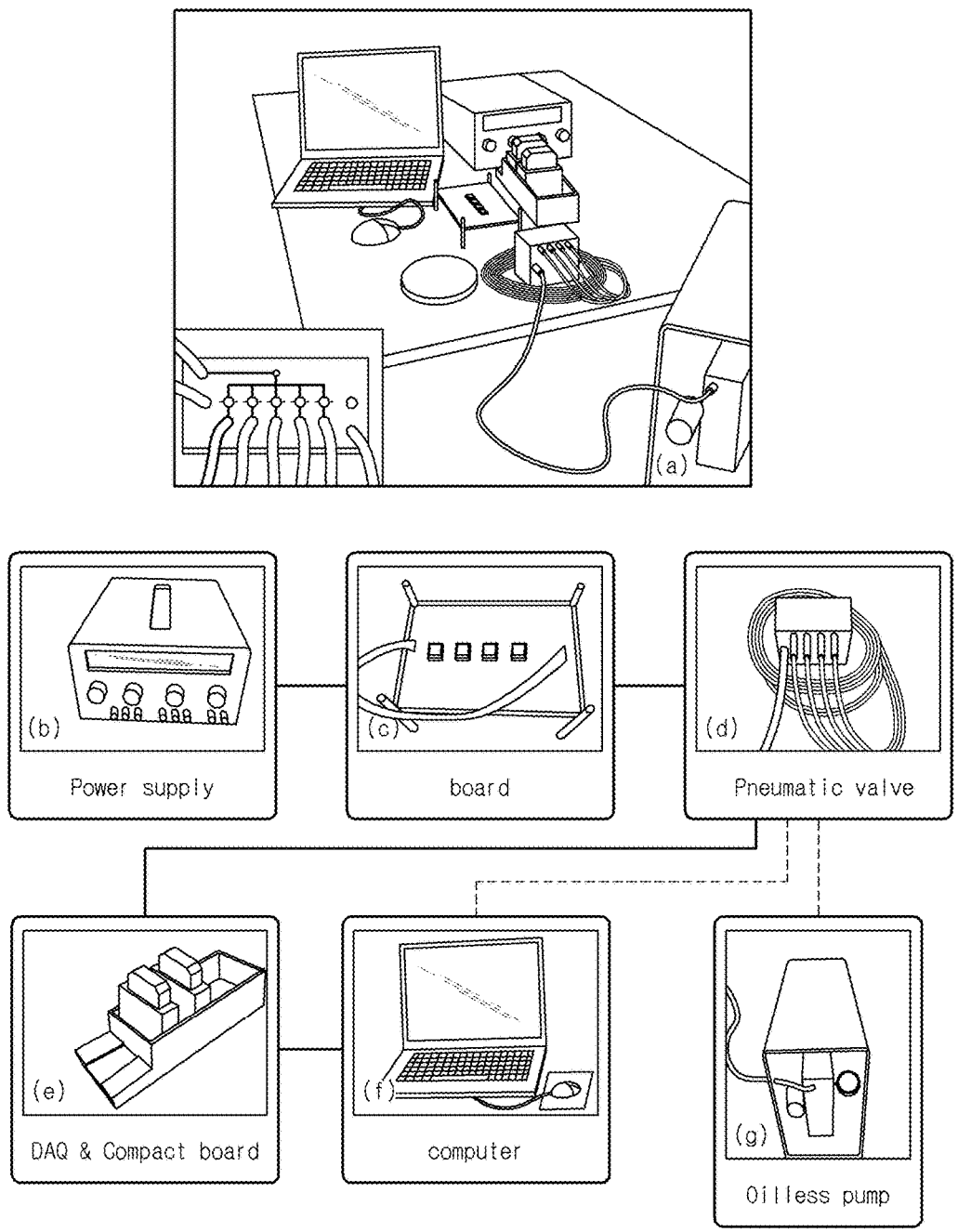
FIG. 6 is a photograph which shows controlling the state of FIG. 4 according to an electrical signal flow.

FIG. 6 shows the state of an experiment employing a pneumatic valve in terms of electromechanical signal flows. Pneumatic pressure (P) mechanically inputted into a chamber using an automatic pneumatic system that is controlled by an electrical signal by mouse or keyboard input induces the deformation of the diaphragm of a chamber array, and this deformation (δ) serves as a valve for preventing a flow from flowing.

In addition, the multiplex microfluidic device for aptamer selection according to the present invention can be designed as shown in FIGS. 7 to 10.

Figure 7:
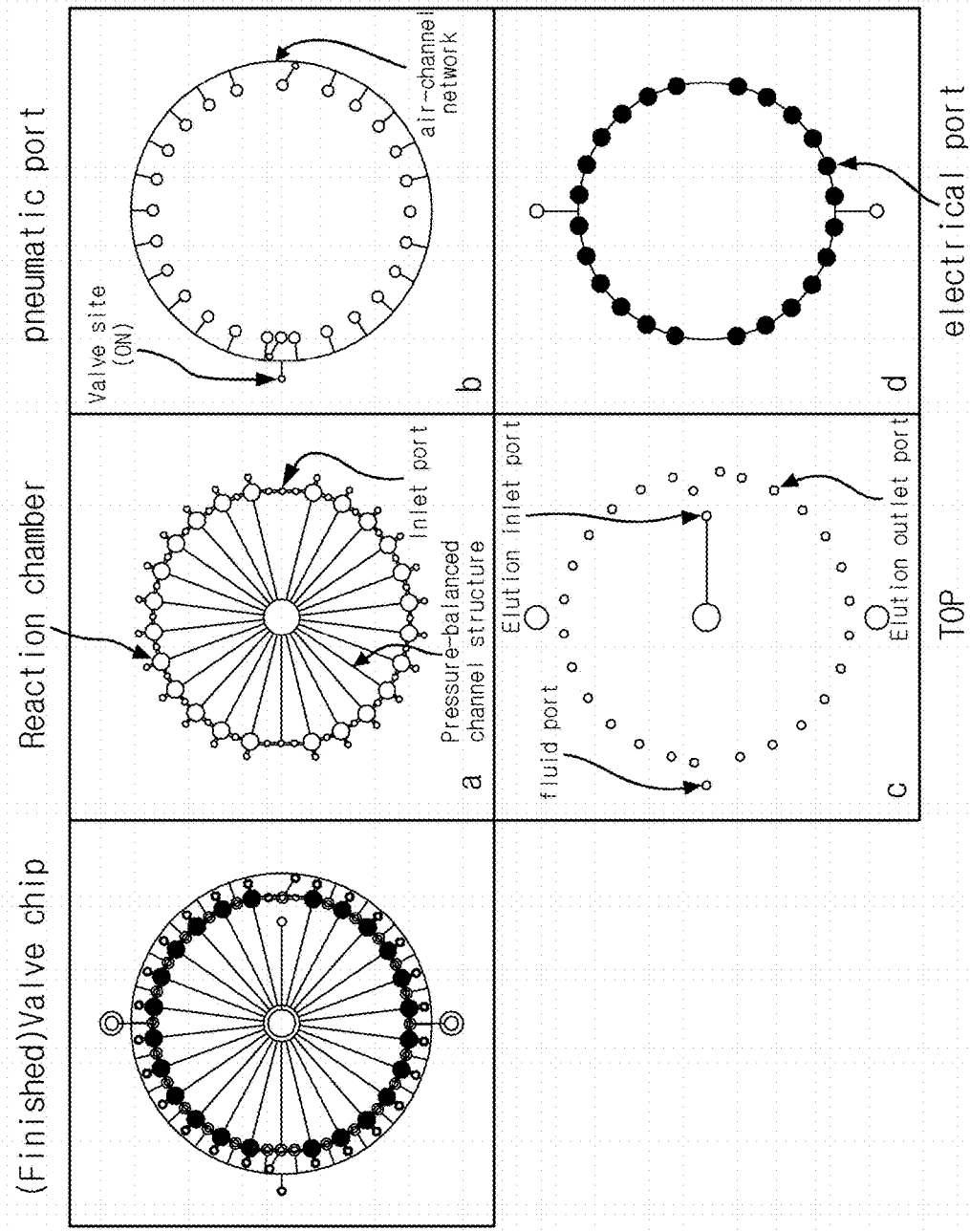
FIG. 7 shows an embodiment of a disc-type 24-multiplex SELEX chip.

FIG. 7 shows a 24-multiplex SELEX chip having a simple disc shape. This chip allows simultaneous elution like a fountain and can increase efficiency. Particularly, it enables a larger number of SELEX to be performed, because several chambers can be provided in the disc shape. Preferably, a pump is provided in the chip so that SELEX can be automatically performed.

Figure 8:
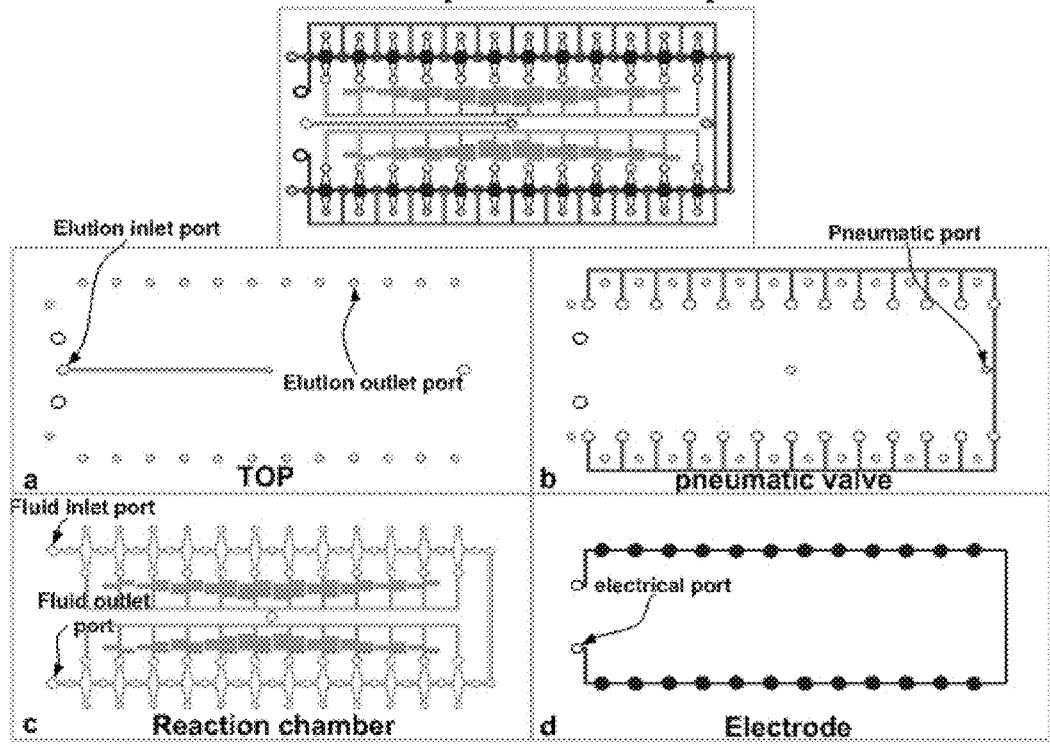
FIG. 8 shows an embodiment of a 24-multiplex SELEX chip.

FIG. 8 also shows a 24-multiplex SELEX chip, and in this case, about 6 chips can be constructed on one mold, and thus several chips can be constructed at the same time, and the efficiency of experiments can be increased. When the chip size is increased, a 24 or more multiplex SELEX chip can be constructed, and the chambers have an independent shape, and thus have no influence on the surrounding sol-gel.

Figure 9:
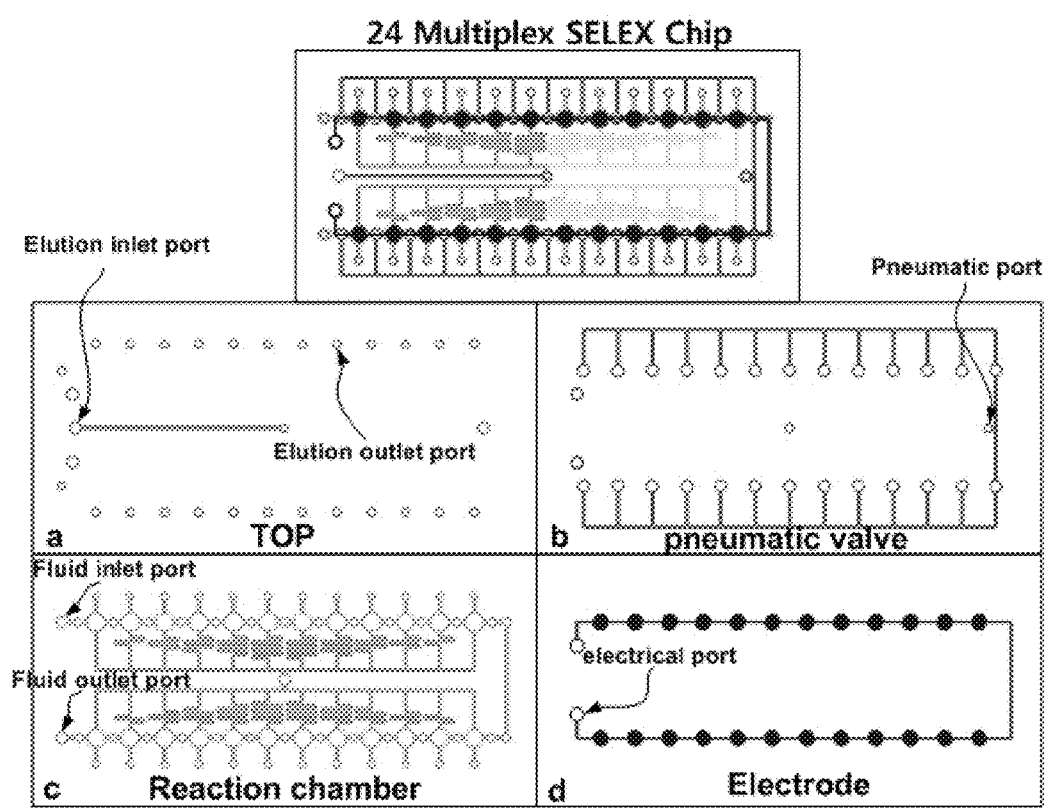
FIG. 9 shows an embodiment of a 24-multiplex SELEX chip.

In addition, FIG. 9 also shows a 24-multiplex SELES chip. In this case, when the chip size is increased, a 24 or more multiplex SELEX chip can be constructed.

Figure 10:
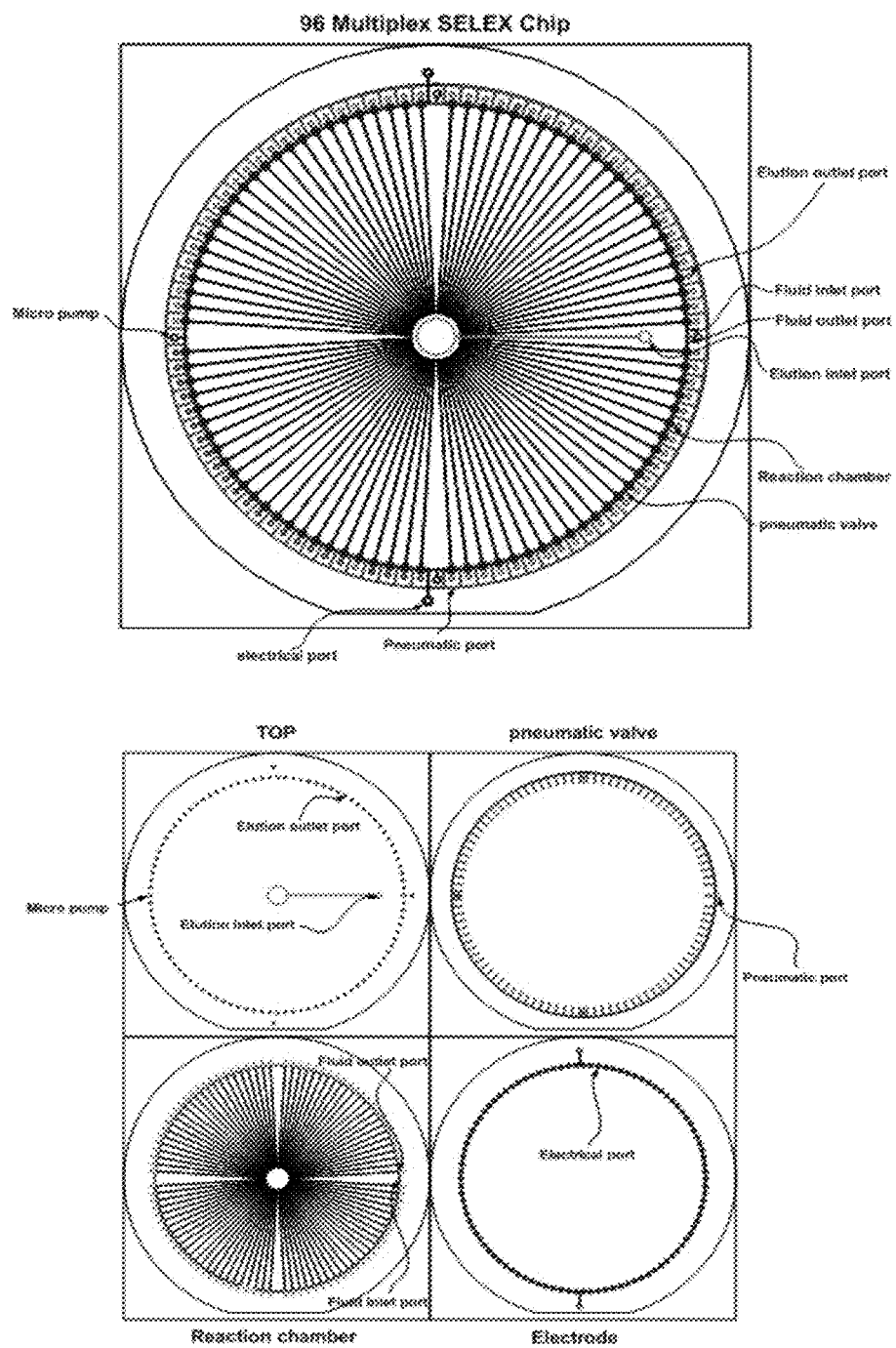
FIG. 10 shows an embodiment of a disc-type 96-multiplex SELEX chip.

Meanwhile, FIG. 10 shows a 96-multiplex SELEX chip which is a simple disc-type chip. This chip can be designed to have a small size. This enables simultaneous elution like a fountain, and thus the efficiency of experiments can be increased. Particularly, it enables a larger number of SELEX to be performed, because several chambers can be provided in the disc shape. Preferably, a pump is provided in the chip so that SELEX can be automatically performed.

The present invention is also directed to a multiplex microfluidic device for selection of aptamers, which comprise:

(a) a substrate comprising a binding channel that connects an inlet port to an outlet port;

(b) a plurality of target molecule-binding regions formed in the binding channel; and (c) a connection region that connects the plurality of target molecule-binding regions to each other.

Figure 11:
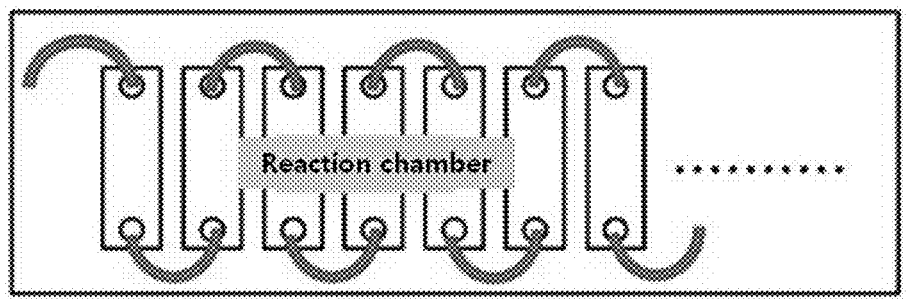
FIG. 11 is a schematic view showing a microfluidic device comprising target-binding regions (reaction chambers) connected to each other by a connection region (i.e., tube).
Figure 12:
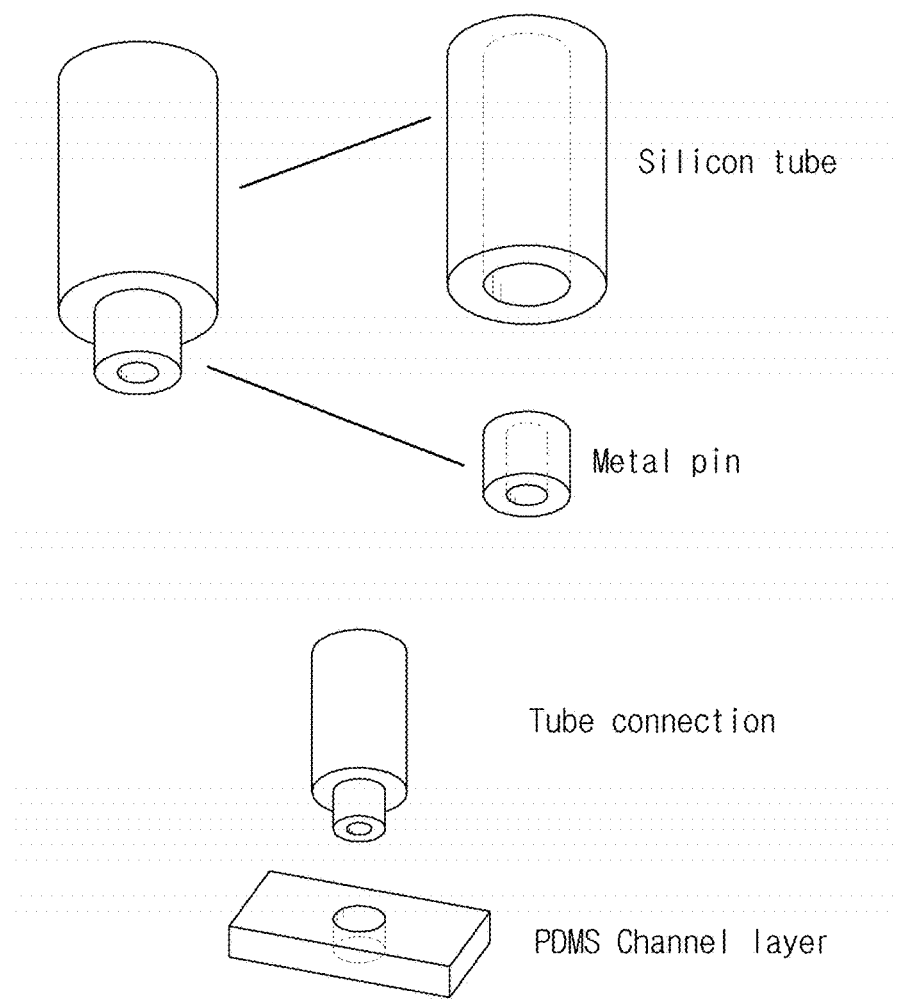
FIG. 12 is a schematic view showing that a metal pin is used between a tube and a channel layer when target-binding regions are connected to each other by a connection region (i.e., tube).

In the present invention, one end of the connection region can be isolated from one-side or both-side target molecule-binding region, and the connection region may be a tube as shown in FIG. 11. In the present invention, the binding channel and the target molecule-binding regions may be formed by a substrate lid which is deposited on the surface of the substrate, and the tube may be connected to the hole of each target molecule-binding region formed by the substrate lid which is deposited on the chip surface. Herein, a method such as "direct connection between the tube and the hole of the target molecule-binding region", "direct connection between the needle of a Hamilton syringe and the hole of the target molecule-binding region" or the like can be used, but in this case, there are problems, such as leakage of reactants, and impossible recycling. To overcome these problems, in the present invention, as shown in FIG. 12, a metal pin is connected to the cut portion of the tube for connection between the target molecule-binding regions, that is, the chambers in which a binding reaction occurs, so that the connection of the tube to the chamber inlet and the separation of the tube can be easily performed and the connection structure can be continuously used.

Figure 13:
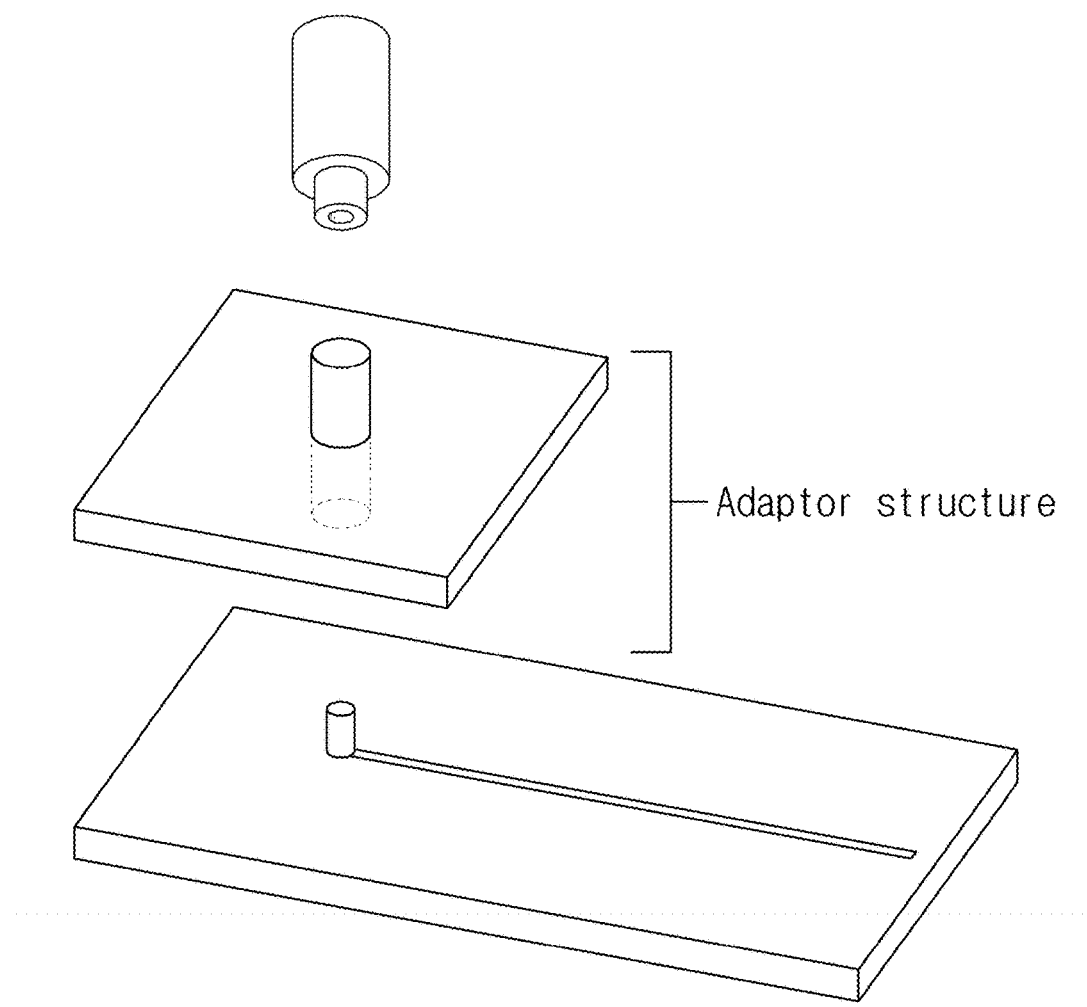
FIG. 13 is a schematic view showing that an adaptor structure is used when target-binding regions are connected to each other by a connection region (i.e., tube).

In addition, in an embodiment of the present invention, in order to prevent the substrate lid forming the hole of the target molecule-binding region from coming off from the substrate, as shown in FIG. 13, an adapter structure may additionally be deposited. Herein, the adapter structure may be a sheet-type structure made of PDMS (polydimethylsiloxane). When the adaptor structure is provided, the connection between the tube and the channel layer is enhanced so that the strong adhesion between the substrate surface and the substrate lid is induced.

In the device according to the present invention, there is an advantage in that target molecules can be fixed to target molecule-binding regions, that is, reaction chambers, using various methods. Illustratively, various materials can be fixed using a sol-gel method. For example, chemical compounds, low-molecular-weight materials, proteins, antibodies, cells or the like may be fixed to the reaction chambers in an active state without structural changes. In addition, Ni-NTA-agarose beads, magnetic beads, glutathione-treated beads, materials reacting with epoxy resin, and bead complexes can be fixed to the reaction chambers, and other kinds of beads can be fixed when various kinds of target molecules are used. Further, as different types of cells can be fixed to the reaction chambers, aptamers about materials that are expressed on the cell surface can be developed.

Preferably, a membrane filter can be used in order to prevent the target molecule-binding regions (i.e., reaction chambers) from contaminated by each other or the target molecule and the bead complex from being mixed with each other. In other words, when the PDMS lid is constructed, two kinds of reagents are mixed, the membrane is attached to the hole portion to which the tube is to be connected, and a hole is formed through the cured membrane and connected with the tube. In this manner, it is possible to prevent the chambers from being contaminated by each other. Accordingly, the present invention is characterized in that a filter is further disposed between the target molecule-binding regions.

Nucleic acids bound to the target molecules of the target molecule-binding regions can be eluted to the elution channels by the valve on/off system or eluted through one end of the connection region of the target molecule-binding regions. The separation of the nucleic acids bound to the target molecules may be applied directly to chips developed by various methods depending on the materials fixed to the reaction chambers. Illustratively, the nucleic acids can be separated by changing the three dimensional structure of the nucleic acids using methods such as high-concentration salt treatment (NaCl, KCl, $MgCl_2$, Tris, etc.), pH changes (HCl or NaOH treatment), and the nucleic acids can be separated by inducing the structural change of the target proteins by urea treatment. In addition, as a competitive separation method using a change in concentration, treatment with high-concentration imidazole or glutathione may be used to induce competitive separation/binding. In the case of separation of nucleic acids using chemicals, the nucleic acids are separated by inducing nucleic molecule binding competition by treatment with high-concentration chemicals.

However, in an embodiment of the present invention, the nucleic acids bound to the target molecules were separated using heat. An aptamer has a binding affinity for a target substance by forming a structure, in which the structure is formed by a hydrogen bond between bases. The temperature that cause the thermal denaturation of DNA or RNA is referred to as dissolution temperature, and at a temperature slightly higher than the dissolution temperature, a hydrogen bond between bases is broken so that the structure of the aptamer is broken and loses binding affinity for the target material, and thus can be eluted from the target. Generally, the aptamer is eluted at 65~95° C.

Accordingly, in a SELEX-on-a-chip constructed in one embodiment of the present invention, a metal electrode was deposited on the chip to make a structure having increased resistance so that an aptamer could be eluted by generating high heat. Elution of highly pure aptamers was induced by optimizing thermal conditions (investigating temperature conditions that influence only the structural change of aptamers). Preferably, a conventional method may be applied together with heat generated in the chip.

In the device according to the present invention, one electrode as a heater may be disposed near the plurality of target molecule-binding regions, or the plurality of electrodes may also be individually disposed near the target molecule-binding regions. In the case of PCT/US2009/054097 filed in the name of the present inventors, electrodes are required to be individually formed on the bottoms of target molecule-binding regions so that nucleic acids bound to the target molecules of the target molecule-binding regions formed in one fluid channel are sequentially eluted without being mixed with each other, whereas the device according to the present invention has an advantage in that nucleic acid molecules can be eluted by heating all the target molecule-binding regions using one electrode. Herein, the metal electrode may be made of any material (e.g., Al, Cr/Au, etc.) that generates heat. Particularly, this advantage geometrically decreased the time when a large number of target molecules were simultaneously subjected to SELEX as shown in FIGS. 8 to 10. In the previous patent, high-throughput selection of 24-plex or more could not be realized due to inefficient elution time, but the present invention increases the efficiency of high-throughput selection by the on/off system of the valve system, making it possible to perform multiplex analysis such as 24-plex, 96-plex and the like.

Also, the present invention provides the following improvements in order to prevent the leakage of reactants during valve driving and tube connection. Specifically, in an embodiment of the present invention, the leakage of fluids could be minimized by controlling and optimizing the flow rate and flow of fluids to reduce the pressure in the adhesion portion between the substrate lid and the substrate (chip). Also, the glass substrate surface was coated with PDMS (polydimethylsiloxane), and the substrate lid for forming the chambers and the channels was also made of PDMS to make "all-PDMS chip", and as a result, the adhesion between the chip and the substrate lid increased after plasma cleaning to minimize the leakage of fluids. In other words, in the present invention, the chip may be formed of any one of plastic materials, such as PDMS, PMMA (polymethylmethacrylate) and polystyrene, glass, silicon and metals such as gold. Preferably, the substrate may be coated with PDMS (polydimethylsiloxane). Herein, the substrate lid is formed of PDMS (polydimethylsiloxane) to construct a all-PDMS chip. In addition, the substrate is preferably coated with a compound, such as polyvinyl acetate (PVAc), which can facilitate the immobilization of target molecules onto the substrate.

In an embodiment of the present invention, the substrate lid was made of PDMS, and the thickness of the substrate lid was controlled so as to reduce back pressure which occurs in the channels in the absence of the flow of fluids. In addition, the efficiency with which the valve is driven can be increased by making the thickness of the PDMS lid thin. Specifically, the thickness of the PDMS lid is preferably 200 µm or less, and more preferably 100-200 µm.

Meanwhile, the substrate lid may be formed of polystyrene, and the substrate may be formed of a plastic material, glass or silicon, thereby preparing a device made of plastic-polystyrene, glass-polystyrene or silicon-polystyrene.

The multiplex microfluidic device may be used as a unit (module), and two or more multiplex microfluidic devices may be connected to each other and used. Thus, in another aspect, the present invention is directed to a multiplex chip for selection for aptamers, which comprises two or more microfluidic devices as described above as a module, wherein the modules are connected to each other by a connection region. In this case, the modules may be connected to each other in series or in parallel by a tube or a channel to make a multiplex chip. In addition, a filter is additionally provided in the connection region that interconnects the modules, thereby preventing the modules from being contaminating by each other.

In still another aspect, the present invention is directed to a method for high-throughput selection of nucleic acid aptamers using the multiplex microfluidic device, which comprises the steps of:

(a) introducing a pool of single stranded nucleic acids having randomized sequences into the binding channel of the above multiplex fluidic device to react with target molecules of target molecule-binding regions in the binding channels;

(b) removing nucleic acids, unbound to the target molecules, from the multiplex fluidic device;

(c) eluting nucleic acids, bound to the target molecules, to elution channels or one end of a connection region in the multiplex fluidic device;

(d) collecting and amplifying the nucleic acids eluted in step (c);

(e) introducing the nucleic acids, amplified in step (d), into the binding channel of the multiplex fluidic device, and repeatedly performing steps (a) to (d), wherein amplification of the eluted nucleic acids is not performed in a final repeat round; and (f) selecting nucleic acids, eluted in the final repeat round, as aptamers.

The method according to the present invention may be applied to a pool of $1\times10^{9-15}$ nucleic acids having different randomized sequences. Randomized is a term used to describe a segment of a nucleic acid having, in principle any possible sequence over a given length. Randomized sequence segments will be of various lengths, as desired, ranging from about eight to more than 100 nucleotides. The chemical or enzymatic reactions by which random sequence segments are made may not yield mathematically random sequences due to unknown biases or nucleotide preference that may exist. The term "randomized" is used instead of "random" to reflect the possibility of such deviations from non-ideality. In the techniques presently known, for example sequential chemical synthesis, large deviations are not known to occur. For short segments, any minor bias that might exist would have negligible consequences.

Particularly, the method of the invention can include the initial preparation of a test mixture of candidate nucleic acids. The individual test nucleic acids contain a randomized region, which can be flanked by sequences conserved in all nucleic acids in the mixture. The conserved regions are provided to facilitate amplification and selection of nucleic acids. Since there are many such sequences known in the art, the choice of sequence is one which those of ordinary skill in the art can make, having in mind the desired method of amplification. Thus, the nucleic acid can contain subportions that are randomized, along with subportions which are held constant in all nucleic acid species in the mixture. For example, sequence regions known to bind, or selected for binding, to the target protein can be integrated with randomized regions to achieve improved binding or improved specificity of binding. Sequence variability in the test mixture can also be introduced or augmented by generating mutations in the nucleic acids in the test mixture during the selection/amplification process. In principle, the nucleic acids employed in the test mixture can be any length as long as they can be amplified. The method of the present invention is most practically employed for selection from a large number of sequence variants. Thus, it is contemplated that the present method will preferably be employed to assess binding of nucleic acid sequences ranging in length from about four bases to any attainable size.

In the present invention, the target molecules that are included in the target molecule-binding regions of the multiplex microfluidic device may be the same target molecules or two or more different target molecules. Preferably, the target molecules may be different target molecules, and in this case, the target molecule-binding region, that is, a chamber in which the target molecule binds to the introduced nucleic acid pool, is connected to other chambers by the binding channel, and thus when a pool of nucleic acids having randomized sequences is added to the inlet port of the binding channel, the nucleic acid pool can enter each chamber and bind to several nucleic acid molecules. Thus, the competition of aptamers for each target molecule can be induced so that aptamers having high affinity can be screened.

This target molecule may be may be a protein or polypeptide, a carbohydrate, a lipid, a pharmaceutical agent, a low-molecular-weight material, an organic non-pharmaceutical agent, or a macromolecular complex such as a cell. In addition, any molecule that is targeted by an aptamer may be used as the target molecule.

The nucleic acid pool introduced into the device comes into contact with the target molecules under conditions in which binding to the target molecules is preferred. Among the nucleic acid pool, nucleic acid that can bind specifically bind to the target molecules binds to the target molecules to form nucleic acid-target molecule pairs. Thus, unbound nucleic acids that follow can be removed.

Meanwhile, as used herein, the term "amplifying" means any process or combination of process steps that increases the amount or number of copies of a molecule or class of molecules. Herein, the amplification process may be a PCR process. Thus, it may include making cDNA copies of selected RNAs, using polymerase chain reaction to increase the copy number of each cDNA, and transcribing the cDNA copier to obtain RNA molecules having the same sequences as the selected RNAs. Specifically, any reaction or combination of reactions known in the art can be used as appropriate, including direct DNA replication, direct RNA amplification and the like, as will be recognized by those skilled in the art. The amplification method should result in the proportions of the amplified mixture being essentially representative of the proportions of different sequences in the initial mixture.

In addition, in the method of the present invention, the multiplex microfluidic device may be used as a unit (module), and two or more multiplex microfluidic devices may be connected to each other and used. In this case, the modules may be connected to each other in series or in parallel by a tube or a channel to make a multiplex chip. Illustratively, 24 4-plex chips may be connected to each other to provide a 96-well plate-type chip. When such modules are used, an experiment may be performed using a well-type chip having several tens to hundreds of wells, and the chip can be easily applied directly to sequencing (e.g., Solexa) or analysis of binding affinity between materials (e.g., Octet), suggesting that the method of the present invention can be performed in an automated manner.

In addition, step (e) of repeatedly performing steps (a) to (d) is repeatedly performed until a selected goal is achieved. For example, step (e) can be continued until a desired level of binding of nucleic acids among the initial test mixture (i.e., the pool of nucleic acid having randomized sequences) is achieved or until a minimum number of nucleic acid components of the mixture is obtained.

When the multiplex microfluidic device according to the present invention is used, the selection of aptamers is possible even when up to 6 repeat rounds are not performed. In other words, the repeating step may be performed less than 6 times. Preferably, it may be performed 1 to 3 times.

Meanwhile, in each repeat round, nucleic acids eluted from the multiplex microfluidic device are sequenced by high-throughput sequencing, the sequences obtained by high-throughput sequencing in the repeat rounds are compared with each other, and nucleic acids whose relative ratio increases with an increase in the number of the repeats may be selected as aptamers. When the high-throughput sequencing method is used, cloning does not need to be performed, and thus aptamers can be selected in a faster and simpler manner. In other words, the number of SELEX steps can be reduced using bioinformatics analysis tools.

A system for performing this high-throughput sequencing method may be connected to one end of each elution channel or each connection region of the multiplex microfluidic device, so that the sequencing can be immediately performed. In the prior art, aptamers for targets were selected, and then cloned into T-vectors and sequenced separately. Thus, there were problems in that cloning is troublesome, aptamers could necessarily be individually sequenced, and many aptamers in multiplex SELEX should be sequenced separately. In an embodiment of the present invention, a pool of aptamers can be simultaneously sequenced using Solexa high-throughput sequencing without having to perform cloning. In addition, aptamers for various targets or an aptamer pool for each SELEX round can be simultaneously sequenced using an adaptor having individual barcodes. At present, technology capable of sequencing aptamers for 96 targets or each round using 96 barcodes is known. Examples of the high-throughput sequencing method include Solexa, Solid techniques, etc. In addition, any technique capable of sequencing a large number of sequences in high throughput may be used in the present invention without limitation.

In addition, step (f) may comprise performing a target molecule affinity test on the finally eluted nucleic acids and selecting nucleic acids having affinity as aptamers. The target molecule affinity test may be a high-throughput affinity test. Illustratively, the target molecule affinity test may be performed using an Octet system. The Octet system BLI (Bio-Layer Interferometry) is a system capable of performing label-free kinetic analysis and quantitation for analysis of binding between biomaterials using BLI (Bio-Layer Interferometry) technology. In BLI (Bio-Layer Interferometry) is technology, a change in the thickness of the sensor surface occurs when the binding between materials on the optical layer of the sensor surface occurs, and this change in the thickness is expressed as the change in the wave pattern of white light which reflects the sensor, and the binding between the materials is measured based on the change in the wave pattern. Thus, a kinetic selection or affinity test for 96 samples can be performed within 2 hours, suggesting that multiplex analysis is possible. In addition, the interaction between not only proteins, but also peptides or low-molecular-weight materials can be measured. Further, because the sensor does not need to be labeled, it is used in an easy and simple manner. Also, it directly detects the surface of samples, unlike other label-free technologies, and thus it appears that various problems occurring fluid systems are eliminated. Accordingly, a 96-well plate type device can be provided based on the microfluidic device according to the present invention and may be connected to the Octet system.

Figure 15:
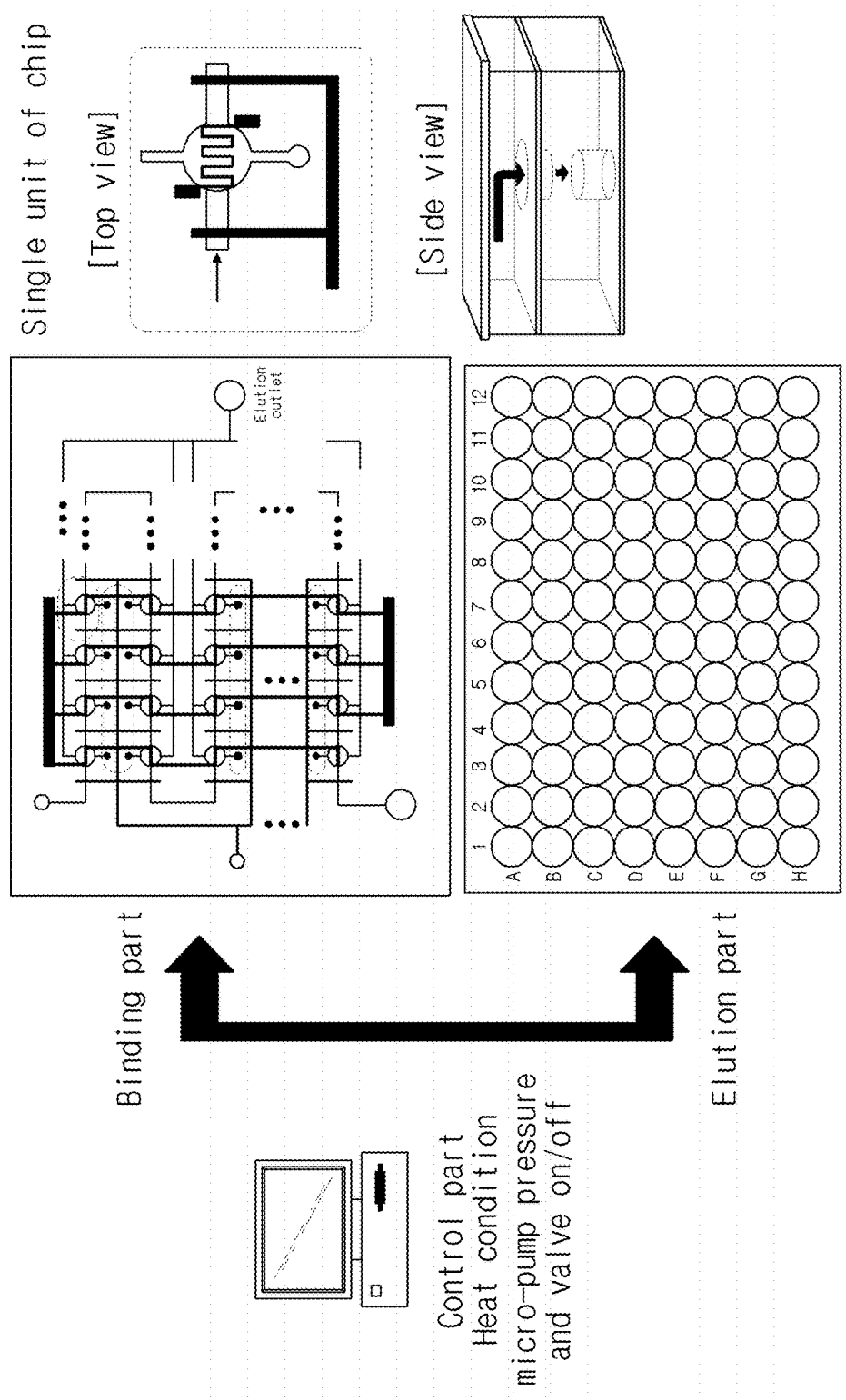
FIG. 15 is a schematic view illustrating that a method according to the present invention is automatically performed.

Thus, as shown in FIG. 15, each step of the method according to the present invention can be performed in an automated manner. Conventional SELEX processes are a collection of bio-related experiments, and the success of the experiments was determined depending on the ability and know how of the experimenters in each step. Thus, there has been a high demand for the standardization and automation of the SELEX processes.

However, the device according to the present invention is a SELEX-on-chip and can be designed according to the standards of general 96/384-well plates so that it can be connected to conventional systems to automate the overall SELEX process. In addition, the device of the present invention that is a SELEX-on-a-chip is constructed in a module form, and thus a plurality of the modules can be connected to each other in series or parallel by a tube to make multiplex chips (e.g., 96-well type, 384-well type, etc.). Further, the device of the present invention can be physically connected to a standardized SELEX chip using a tube, or the chambers can be opened or closed using the valve system, and thus the elution and recovery of aptamers in a 96-well plate can be controlled in an automated manner. Thus, the device of the present invention can be easily applied to conventional 96/384-well plate-based systems (PCR, High Throughput sequencer, affinity measurement systems, etc.).

In an embodiment of the present invention, the following five aptamers for BSA (negative control), TBP, IIB, EGFP and HSF were isolated using the 5-plex microfluidic device of FIG. 2: 101apt (TBP targeting aptamer), b4apt (IIB targeting aptamer), GFPapt (EGFPfmf targeting aptamer) and HSFapt (HSF targeting aptamer). Then, in order to examine whether the aptamers eluted according to the device and method of the present invention bind to the corresponding targets, Q-PCR was performed using StepOne-Plus RT PCR (Applied Biosystems).

Figure 16:
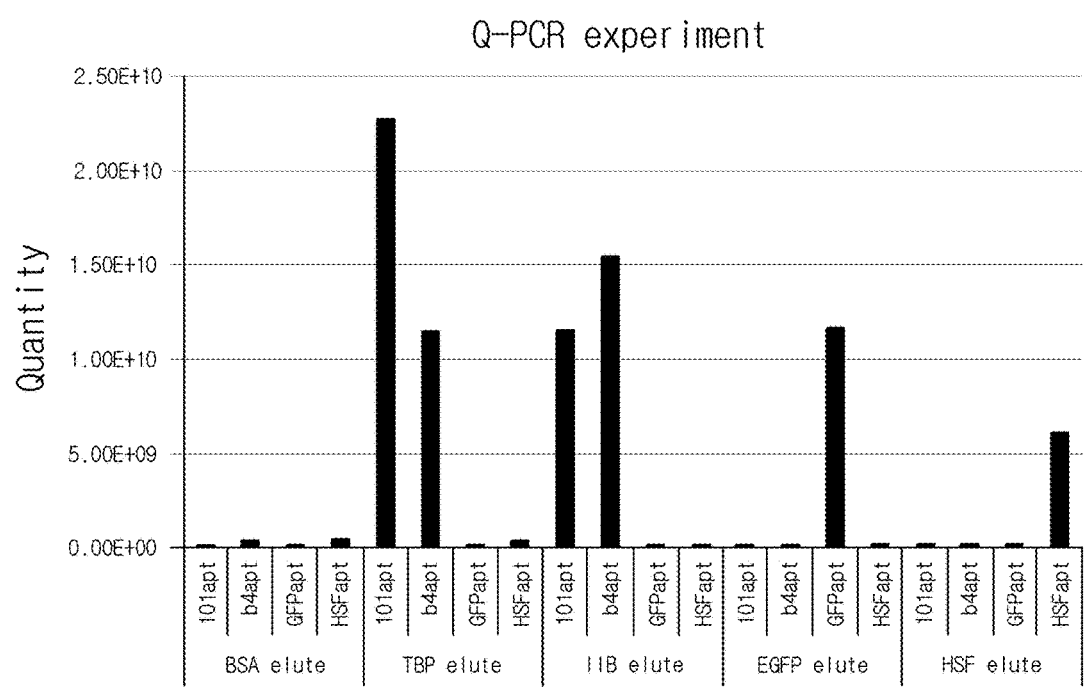
FIG. 16 is a graphic diagram showing the results obtained by isolating aptamers for five kinds of targets, including BSA (negative control), TBP, IIB, EGFP and HSF, using the device of FIG. 2, and performing a Q-PCR experiment to determine whether or not each aptamer binds to the corresponding target.

As a result, as shown in FIG. 16, the eluted aptamers targeting TBP, IIB, EGFP and HSF had high affinities for their targets. In FIG. 16, higher quantity at the Y-axis indicates higher affinity.

Meanwhile the method according to the present invention may be provided in the form of a kit to increase portability. That is, in yet another aspect, the present invention is directed to a kit for high-throughput selection of aptamers, which comprises the above multiplex microfluidic device. Herein, the kit may include reagents for the amplification and sequencing of eluted nucleic acids in a separate container or reaction unit.

The kit for high-throughput selection of aptamers may take the form of bottles, tubs, sachets, envelops, tubes, ampoules, and the like, which may be formed in part or in whole from plastic, glass, paper, foil, wax, and the like. The container may be equipped with a fully or partially detachable lid that may initially be part of the container or may be affixed to the container by mechanical, adhesive, or other means. The container may also be equipped with a stopper, allowing access to the contents by a syringe needle. The kit may comprise an exterior package which may include instructions regarding the use of the components.

INDUSTRIAL APPLICABILITY

As described above, the present invention provides a multiplex microfluidic device for selecting nucleic acid aptamers and a method for high-throughput selection of nucleic acid aptamers using the same. The multiplex microfluidic device according to the present invention can simultaneously detect aptamers for a plurality of targets, and it can greatly increase the screening throughput and greatly shorten the process time compared to conventional multiplex techniques. Particularly, when a process for selecting aptamers is performed using the inventive device together with a high-throughput sequencing method, the number of target binding/elution/amplification rounds can be greatly reduced, and the process can be performed in an automated manner. Thus, the device of the present invention is highly useful.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A multiplex microfluidic device for simultaneous isolation of nucleic acid aptamers for a plurality of target molecules, comprising:
    (a) a substrate lid portion comprising a thickness of 200 micrometers or less in which a plurality of target molecule-binding regions, a binding channel, a connection region, and a valve system are formed, wherein the substrate lid portion comprises;
        (i) a first polymer layer comprising;
            (1) a binding channel that connects an inlet port to an outlet port;
            (2) a plurality of target molecule-binding regions connected by the binding channel, the plurality of target molecule-binding regions comprising target molecules bound to nucleic acid aptamers, wherein the target molecules selectively bind the nucleic acid aptamers that are flowed through the binding channel and into the plurality of target molecule-binding regions, and wherein the plurality of target molecule-binding regions and target molecules are constructed and arranged such that the nucleic acid aptamers bound to each of the target molecules in the plurality of target molecule-binding regions are simultaneously elutable in bound form from each of the plurality of target molecule-binding regions by heat-driven elution; and (3) a plurality of separate elution channels directly connected to each of the plurality of target molecule-binding regions, such that each of the plurality of separate elution channels and each of the plurality of target molecule-binding regions are configured for simultaneous flow of nucleic acid aptamers bound to target molecules from each of the plurality of target molecule-binding regions in which binding has taken place through each of the separate elution channels with which each of the plurality of target molecule-binding regions is directly connected, whereby nucleic acid aptamers for a plurality of target molecules are simultaneously isolatable in the plurality of elution channels upon said heat-driven elution; and (4) a connection region that connects each of the plurality of target molecule-binding regions to each other;

(ii) a second polymer layer comprising valve system comprising; a binding channel fluid flow valve in the binding channel to separate the binding channel between the plurality of target molecule-binding regions and arranged to control flow in the binding channel of fluid containing a multiplicity of the nucleic acid aptamers introduced to the binding channel for flow through each of the plurality of target molecule-binding regions in the binding channel; and (iii) a third polymer layer comprising an eluting valve connected to each of the plurality of separate elution channels and arranged to control the flow of fluid containing the nucleic acid aptamers bound to target molecules from each of the plurality of target molecule-binding regions to each of the plurality of separate elution channels, such that the nucleic acid aptamers bound to target molecules are simultaneously flowed from each of the plurality of target molecule-binding regions in which binding has taken place to each of the plurality of separate elution channels with which the target molecule-binding regions are respectively directly connected;

(b) a substrate base portion comprising a polymer coating and a single metal electrode heater comprising one electrode in a pattern extending over the substrate base portion in registration and heating relationship with all of the target-molecule-binding regions of the device, and constructed and arranged to simultaneously heat all of the plurality of target molecule-binding regions after binding has taken place therein, wherein upon heating and operation of the valve system, the nucleic acid aptamers bound to target molecules in the plurality of target molecule-binding regions simultaneously elute in bound form from each of the plurality of target molecule-binding regions and into each of the plurality of separate elution channels.

2. The multiplex microfluidic device of claim 1, wherein the binding channel and the plurality of target molecule binding regions are formed by the substrate lid portion when the substrate lid portion is deposited onto the surface of the substrate base portion.

3. The multiplex microfluidic device of claim 1, wherein lengths of the plurality of elution channels are equalized such that that the volume and elution rate of elution solution eluted through the elution channels is constant.

4. The multiplex microfluidic device of claim 1, wherein the one electrode of the single metal electrode heater is made of aluminum, or is made of a combination of chromium and gold.

5. The multiplex microfluidic device of claim 4, wherein the one electrode of the single metal electrode heater is made of aluminum.

6. The multiplex microfluidic device of claim 4, wherein the one electrode of the single metal electrode heater is made of a combination of chromium and gold.

7. The multiplex microfluidic device of claim 2, wherein each polymer layer of the substrate lid portion is formed of PDMS (polydimethylsiloxane).

8. The multiplex microfluidic device of claim 7, wherein the thickness of the substrate lid portion, wherein each layer is formed of PDMS is 100-200 micrometers.

9. The multiplex microfluidic device of claim 1, wherein the substrate base portion comprises a material selected from the group consisting of plastic material, glass, silicon, and a metal.

10. The multiplex microfluidic device of claim 9, wherein the plastic material is selected from the group consisting of PDMS (polydimethylsiloxane), PMMA (polymethylmethacrylate), and polystyrene.

11. The multiplex microfluidic device of claim 9, wherein the substrate base portion is coated with a polymer selected from the group consisting of one of PMMA (polymethylmethacrylate), PVA (Polyvinyl alcohol), and PVAc (polyvinyl acetate).

12. The multiplex microfluidic device of claim 2, wherein the substrate lid portion is formed of polystyrene and the substrate base portion is formed from a material selected from the group consisting of a plastic material, glass, and silicon.

13. The multiplex microfluidic device of claim 1, further comprising a filter disposed between the plurality of target molecule-binding regions.

14. The multiplex microfluidic device of claim 1, wherein one end of the connection region is isolated from the plurality of target molecule-binding region.

15. The multiplex microfluidic device of claim 1, wherein the connection region is a tube.

16. The multiplex microfluidic device of claim 1, wherein the connection region is connected to a hole of each of the plurality of target molecule-binding regions formed by a substrate lid portion which is deposited on the substrate base portion.

17. The multiplex microfluidic device of claim 1, wherein the connection region is connected to a hole of each of the plurality of target molecule-binding regions through a metal pin.

18. The multiplex microfluidic device of claim 1, wherein an adaptor structure is additionally deposited between the connection region and a hole of the plurality of target molecule-binding regions to enhance the adhesion between the substrate lid portion and the substrate base portion.

* * * * *

UNITED STATES PATENT AND TRADEMARK OFFICE
CERTIFICATE OF CORRECTION

PATENT NO.        : 10,221,412 B2                                Page 1 of 1
APPLICATION NO.   : 13/877862
DATED             : March 5, 2019
INVENTOR(S)       : So Youn Kim et al.

It is certified that error appears in the above-identified patent and that said Letters Patent is hereby corrected as shown below:

In the Specification

Column 1, Line 48: "Man-Bock G U" should be -- Man-Bock GU --.

Signed and Sealed this
Sixteenth Day of April, 2019

Andrei Iancu
*Director of the United States Patent and Trademark Office*